United States Patent [19]
Toma et al.

[11] Patent Number: 6,110,475
[45] Date of Patent: *Aug. 29, 2000

[54] COMPOSTION, BARRIER FILM, AND METHOD FOR PREVENTING CONTACT DERMATITIS

[75] Inventors: Joan Dalla Riva Toma, Piscataway; Curtis L. Karl, Somerset, both of N.J.

[73] Assignee: Hydromer, Inc., Branchburg, N.J.

[ * ] Notice: This patent is subject to a terminal disclaimer.

[21] Appl. No.: 09/046,296

[22] Filed: Mar. 23, 1998

Related U.S. Application Data

[60] Division of application No. 08/845,741, Apr. 25, 1997, Pat. No. 5,888,520, which is a continuation-in-part of application No. 08/642,227, Apr. 30, 1996, Pat. No. 5,837,266.

[51] Int. Cl.[7] .............................. A61K 6/00; A61K 7/00; A01N 25/34; A01N 25/00
[52] U.S. Cl. .......................... 424/401; 424/402; 424/404; 424/78.02; 424/78.03; 514/781; 514/862
[58] Field of Search ..................................... 424/401, 402, 424/78.02, 78.03, 404; 514/781, 862

[56] References Cited

U.S. PATENT DOCUMENTS

| | | | |
|---|---|---|---|
| 5,641,513 | 6/1997 | Lech et al. | 424/474 |
| 5,851,540 | 12/1998 | Toma et al. | 424/401 |
| 5,876,754 | 3/1999 | Wunderlich et al. | 424/489 |
| 5,888,520 | 3/1999 | Toma et al. | 424/401 |

*Primary Examiner*—Thurman K. Page
*Assistant Examiner*—Todd D Ware
*Attorney, Agent, or Firm*—Hoffmann & Baron, LLP

[57] ABSTRACT

The present invention relates to a composition, and a method for preventing or reducing contact dermatitis. The composition contains a polysaccharide; a low molecular weight, synergistic saccharide; a solvent; and optionally an additive material.

The present invention is further a dermatologically-compatible barrier film for preventing and reducing contact dermatitis which contains a polysaccharide; a low molecular weight, synergistic saccharide; and optionally one or more additives. The dermatologically-compatible barrier film is formed of a composition containing a polysaccharide; a low molecular weight, synergistic saccharide; a solvent; and optionally an additive material. The composition is a skin care product in a form of a lotion, a gel or a cream that is applied to skin of mammals. Once applied, the solvent in the composition evaporates, and thereby leaving behind a dermatologically-compatible barrier film containing a polysaccharide; a low molecular weight, synergistic saccharide; and optionally an additive material.

16 Claims, No Drawings

COMPOSTION, BARRIER FILM, AND METHOD FOR PREVENTING CONTACT DERMATITIS

This application is a division of U.S. Ser. No. 08/845,741 filed on Apr. 25, 1997 and now U.S. Pat. No. 5,888,520 which is a continuation-in-part of application Ser. No. 08/642,227, filed on Apr. 30, 1996 now U.S. Pat. No. 5,837,266. The present invention relates to a composition and a method for preventing or reducing contact dermatitis. A dermatologically-compatible barrier film for preventing contact dermatitis is also included in the invention.

BACKGROUND OF THE INVENTION

Contact dermatitis is an inflammation of the skin and is an acute or chronic condition resulting from irritation by, or sensitization to, some substance in the environment. In mild cases, the symptoms are itching, burning, or reddening of the skin. In more severe cases, vesiculation and edema may be present and may be followed by weeping and crusting. The most severe cases may be accompanied by bleeding vesicles and gross edema.

Contact dermatitis is typically classified as primary irritant dermatitis or allergic contact dermatitis. Primary irritant dermatitis is the more common form of contact dermatitis. It is normally caused by irritating agents that will cause dermatitis in all persons upon sufficient exposure.

Allergic contact dermatitis may be caused by many substances which induce a reaction in some people upon physical contact. This reaction usually does not occur with the initial contact, but only upon subsequent exposures. More specifically, this reaction creates a hypersensitive state in susceptible individuals. Thus, upon subsequent contact, these individuals will develop contact dermatitis.

In view of the above, contact dermatitis is a serious concern to many people, including industrial workers. Therefore, the need for protection against contact dermatitis is apparent, especially when occupational allergic contact dermatitis can result in lost wages and discomfort to workers.

Attempts have been made to inhibit and treat contact dermatitis. For example, U.S. Pat. No. 4,112,067 to Tomalia et al. disclose a method of treating and controlling dermatitis in humans who have been exposed to allergens produced by plants of the genus Rhus. The method of Tomalia et al. requires topical application of a polyamine polymer having a molecular weight of at least 5000. This does not suggest the present invention.

U.S. Pat. No. 4,451,453 to Lay et al. also discloses a method of controlling and treating dermatitis in humans who have been exposed to allergies produced by plants of the genus Rhus. The method of Lay et al. requires topical application of a cross-linked copolymer of isobornyl acrylate, isobornyl methacrylate, styrene, or alkylstyrene and one or more alkyl esters of a $C_1$ to $C_{20}$ alcohol and acrylic or methacrylic acid. This also does not suggest the present invention.

U.S. Pat. Nos. 3,961,044 and 3,981,990 to Kelly et al, and 4,137,301, 4,141,966, 4,144,319 and 4,160,818 to Willer et al. disclose compositions and methods for preventing or reducing irritation of the skin resulting from allergic contact dermatitis by applying a protective agent. The protective agent of Willer et al. is an organic compound having at least two polar groups separated by a chain of at least 15 carbons. However, these compositions and methods do not disclose or suggest the use of a low molecular weight saccharide that enhances the protection against contact dermatitis.

Accordingly, it is an object of the present invention to provide a composition, a dermatologically-compatible barrier film, and a method for preventing or reducing contact dermatitis.

SUMMARY OF THE INVENTION

The present invention is a composition for preventing or reducing contact dermatitis. The composition contains a polysaccharide; a low molecular weight, synergistic saccharide; a solvent; and optionally an additive material. The composition of the present invention can also include an antimicrobial agent.

The polysaccharide of the present invention is preferably a cellulose derivative.

The low molecular weight, synergistic saccharide is preferably an unmodified monosaccharide, a derivatized monosaccharide, an unmodified disaccharide, a derivatized disaccharide, a hydrolyzed starch, or a derivatized starch hydrolysate.

The solvent is preferably water, lower alcohol, low molecular weight glycol, or mixtures of these.

The additives include any physiologically-psychologically beneficial ingredients that are chemically compatible with the present composition and do not interfere with barrier performance.

The present invention is also a method for preventing and reducing contact dermatitis by applying the above described composition to skin of mammals in an amount effective to prevent contact dermatitis.

The present invention is also a dermatologically-compatible barrier film for preventing or reducing contact dermatitis. The dermatologically-compatible barrier film is formed from a composition containing polysaccharide; a low molecular weight, synergistic saccharide; a solvent; and optionally an additive material.

In a preferred embodiment, the invention includes a dermatologically-compatible, barrier film composition which comprises a hydrophilic, nonionic, film-forming polysaccharide and a barrier film enhancer which by itself has little or no barrier properties and which is comprised of unmodified or derivatized monosaccharides, disaccharides and/or hydrolyzed starch. When dissolved in a dermatologically-compatible solvent and applied to skin, the composition dries to a non-sticky film which reduces or inhibits penetration by natural or synthetic allergenic agents or other skin irritants.

The advantages achieved by the present invention include the use of the low molecular weight, synergistic saccharide to produce a more effective dermatologically-compatible barrier film, which in turn, provides a more effective prevention of contact dermatitis.

In addition, the advantages achieved by the present invention also include the use of antimicrobial agent in the composition to (1) enhance the preservation of the composition; (2) prevent or reduce infection of open or infected skin when applying the composition; and (3) cleanse skin prior to forming an invisible glove for preventing and reducing contact dermatitis.

DETAILED DESCRIPTION OF THE INVENTION

Contact dermatitis can be caused by a variety of irritants. The most widely known natural allergens which are capable of sensitizing and causing contact dermatitis in many people are antigenic plants of the genus Rhus, such as poison ivy, poison oak, and poison sumac.

Other widely known allergens are commercial products such as insecticides containing Pyrethrum or Rotenone, dye intermediates such as aniline, nitro compounds, anthracene, and derivatives thereof, dyes such as paraphenylenediamine and aniline black, photo developers such as hydroquinone and para-amido-phenol, antioxidants such as hexamethylene tetramine, and synthetic and natural resins such as wood rosin and phenol formaldehyde, and detergents and constituents of rubber and latex gloves.

The present invention relates to a composition for preventing or reducing contact dermatitis which includes a polysaccharide; a low molecular weight, synergistic saccharide; a solvent; and optionally an additive material. The composition can also include an antimicrobial agent.

The present invention also involves the application of a dermatologically-compatible barrier film to the skin prior to contact with agents capable of causing allergic contact dermatitis (e.g., plants of the genus Rhus, insecticides, dyes and dye intermediates, etc.) to eliminate or lessen the dermatological reaction.

The dermatologically-compatible barrier film includes a polysaccharide and a low molecular weight, synergistic saccharide. More specifically, the dermatologically-compatible barrier film is derived from a composition containing a polysaccharide; a low molecular weight, synergistic saccharide; a solvent; and optionally an additive material. The dermatologically-compatible barrier film can also be derived from a composition containing a polysaccharide; a low molecular weight, synergistic saccharide; an antimicrobial agent; a solvent; and optionally an additive material.

The composition, in the form of a lotion or a cream, is then applied to skin. Once applied to the skin, the solvent in the composition evaporates, and thereby leaving behind a film containing a polysaccharide; a low molecular weight, synergistic saccharide; and optionally an additive material. The film left behind can also contain a polysaccharide; a low molecular weight, synergistic saccharide; an antimicrobial agent; and optionally an additive material.

The polysaccharide of the present invention is compatible with skin, soluble in solvents, and a good film - former. Preferably, it is a cellulose derivative. The polysaccharides include alkyl derivatives and/or hydroxyalkyl derivatives of cellulose, such as methylcellulose, ethylcellulose, hydroxyethylcellulose, hydroxypropylcellulose, hydroxybutylcellulose, methylhydroxyethylcellulose, methylhydroxypropylcellulose, methylhydroxybutylcellulose, hydroxyethylhydroxypropylcellulose, and ethylhydroxyethylcellulose. More preferably, the polysaccharide is a hydroxypropylcellulose. The degree of polymerization (DP) of the polysaccharide is not critical, but, should be high enough to provide good film-forming properties yet low enough to provide flowable solutions which are easily applied to skin. The cellulose derivatives of the present invention are preferably nonionic, linear, polysaccharides. The polysaccharides can be chemically modified by methods known in the art to render them soluble in water or alcohol.

The percentage of the polysaccharide in the composition is about 5 wt. % to about 20 wt. %, and preferably, about 15 wt. %.

Low molecular weight, synergistic saccharides used in the invention are comprised of a relatively small number of monosaccharide units as compared with the polysaccharide of the invention. Low molecular weight, synergistic saccharides can be unmodified or derivatized monosaccharides, disaccharides, or hydrolyzed starches which are preferably polar and hydrophilic. Synergistic means that the protective properties of the composition of the invention are greatly enhanced by the presence of the low molecular weight, saccharides which by themselves possess little or no barrier properties.

The low molecular weight, synergistic saccharides of the present invention include an unmodified monosaccharide, a derivatized monosaccharide, an unmodified disaccharide, a derivatized disaccharide, a hydrolyzed starch, or a derivatized starch hydrolysate. The monosaccharide contains 5 or 6 carbons. Disaccharides contain two saccharide units. Derivatized monosaccharides, disaccharides, and starch hydrolysates refer to monosaccharides, disaccharides, and starch hydrolysates that have been produced from other compounds, e.g., in a manner known in the art, preferably by alkoxylation, hydroxyalkylation, or esterification with fatty esters. Hydrolyzed starches include starches that have been modified, e.g., in a manner known in the art.

Some examples of the unmodified monosaccharide are fructose, glucose, and mannose.

Some examples of the unmodified disaccharide are sucrose and maltose.

Some examples of a derivatized monosaccharide are ethoxylates of methyl glucoside, propoxylates of methyl glucoside, propoxylates of methyl glucoside distearate, and methyl glucose dioleate. Preferably, the derivatized monosaccharide is Methyl Gluceth-10 (10 mole ethoxylate of methyl glucoside), Methyl Gluceth-20 (20 mole ethoxylate of methyl glucoside), PPG-10 Methyl Glucose Ether (10 mole propoxylate of methyl glucoside), PPG-20 Methyl Glucose Ether (20 mole propoxylate of methyl glucoside, PPG-20 Methyl Glucose Ether Distearate (20 mole propoxylate of methyl glucoside distearate) or methyl glucose dioleate. The names of the examples of the derivatized monosaccharides described above are standard names of the Cosmetic, Toiletries & Fragrance Association (CTFA). Amerchol Corp., *Amerchol The Elegance Engineer*, (September 1992).

Dextrose Equivalence (DE) is a well known unit of measurement in the starch industry. It is the inverse of the degree of polymerization (DP) and the quantitative measurement of starch polymer hydrolysis. For example, the total hydrolysis that starch can convert to dextrose (glucose) is 100%. Thus, the DE of glucose is 100. The DE of the hydrolyzed starch to be used in the present invention is at least about 4, preferably about 6 to about 100.

Some examples of the derivatized disaccharide and derivatized starch hydrolysate are ethoxylates and propoxylates, such as about 10 mole ethoxylates, about 20 mole ethoxylates, about 10 mole propoxylates, and about 20 mole propoxylates.

Some examples of a hydrolyzed starch are maltodextrin and corn syrup solids. Preferably, the DP of the maltodextrin is from about 1 to about 19 and the DP of corn syrup solids is from about 20 to about 100.

Preferably, the low molecular weight, synergistic saccharide is a derivatized monosaccharide; more preferably, the low molecular weight, synergistic saccharide is Methyl Gluceth-20 (20 mole ethoxylate of methyl glucoside).

The percentage of the low molecular weight, synergistic saccharide in the composition is about 2 wt. % to about 10 wt. %, and preferably, about 5 wt. %.

Antimicrobial agents that can be used in the present invention are compatible with skin and soluble in solvents. In addition, antimicrobial agents are active against a broad spectrum of microorganisms, including but are not limited to, gram positive and gram negative bacteria, yeast, and mold. Examples of the antimicrobial agents include, but are not limited to, triclosan (5-chloro-2-(2,4-dichlorophenoxy) phenol which is also known as Irgasan™ DP 300 manufactured by Ciba-Geigy Corporation), hexetidine (5-amino-1,3-bis(2-ethylhexyl)-5-methyl-hexahydropyrimidine), chlorhexidine salts (salts of N,N"-Bis(4-chlorophenyl)-3,12-diimino-2,4,11,14-tetraazatetradecanediimidiamide), 2-bromo-2-nitropropane-1,3-diol, hexyresorcinol, benzalkonium chloride, cetylpyridinium chloride, alkylbenzyldimethylammonium chlorides, iodine, phenol derivatives, povidone-iodine (polyvinylpyrrolidinone-iodine), parabens, hydantoins (2,4-imidazolidinedione), hydantoins derivatives (derivatives of 2,4-imidazolidinedione), phenoxyethanol, cis isomer of 1-(3-chloroallyl)-3,5,6-triaza-1-azoniaadamantane chloride (quarternium-15 which is also known as Dowicil 200 manufactured by Dow Chemical Company), diazolidinyl urea, benzethonium chloride, methylbenzethonium chloride, and mixtures thereof. Examples of hyndantoin derivatives include, but are not limited to, dimethylol-5,5-dimethylhydantoin (glydant). Preferably, examples of the antimicrobial agents include triclosan, cis isomer of 1-(3-clhoroallyl)-3,5,6-triaza-1-azoniaadamantane chloride (quarternnium-15), hyndantoins, hyndantoin derivatives such as dimethylol-5,5-dimethylhydantoin (glydant), and mixtures thereof.

The percentage of the antimicrobial agents in the composition is about 0.01 wt. % to about 10 wt. %, and preferably, about 0.01 wt. % to about 2 wt. %.

Solvents to be used in the invention are preferably compatible with skin, capable of drying in a reasonable amount of time, and capable of dissolving the solid ingredients of the composition.

The solvent of the present invention includes water, lower alcohols, low molecular weight glycols, or mixtures of these. Lower alcohols refer to $C_1$ to $C_4$ alcohols. Some examples of the lower alcohol are methanol, ethanol, 1-propanol, 2-propanol, and butanol. Some examples of the low molecular weight glycols are glycerol and propylene glycol. Preferably, the solvent is water, lower alcohol, low molecular weight, glycol, or mixtures thereof. The solvent of the invention can be chosen to have the ability to penetrate into the skin.

The percentage of the solvent in the composition is about 70 wt. % to about 93 wt. %, and preferably, about 80 wt. %.

The additive material includes any physiologically-psychologically beneficial ingredients compatible with the composition of the present invention. Known physiologically-psychologically beneficial additive materials include colorants, fragrances, sunscreen, insect repellants, surfactants (wetting agents), flow modifiers (rheology modifiers), cleansers, moisturizers, film solubility modifiers, film plasticizers, salts, natural extracts, and mixtures thereof that do not interfere with barrier performance. In addition, the additive agent also includes exfoliants, astringents, antioxidants, vitamins, self-tanning gents, emulsifiers, emollients, enzymes, keratolytics, antipruritics, analgesics, anesthetics, antihistamines, antimicrobials, preservatives, antibiotics, antiseptics, antifungals, antivirals, other biologically active agents, and mixtures that do not interfere with barrier performance.

The percentage of the additive material in the composition is about 0.01 wt. % to about 30 wt. %, and preferably, about 1 wt. % to about 20 wt. %.

The composition of the present invention can be formulated into skin care products, such as cosmetics and moisturizers in the form of a lotion, a gel, or cream. The preferred embodiment may be considered a pre-exposure lotion which protects the skin against allergens such as poison ivy, oak, sumac, and other irritants.

The present invention is also a method for preventing or reducing contact dermatitis by applying to skin of mammals a dermatitis-preventing effective amount of a composition containing a polysaccharide; a low molecular weight, synergistic saccharide; a solvent; and optionally an additive material. The method of the present invention can also include applying to skin of mammals a dermatitis-preventing effective amount of a composition containing a polysaccharide; a low molecular weight, synergistic saccharide; an antimicrobial agent; a solvent; and optionally an additive material.

The present invention is further a dermatologically-compatible barrier film for preventing or reducing contact dermatitis. The dermatologically-compatible barrier film is formed of a composition containing a polysaccharide; a low molecular weight, synergistic saccharide; a solvent; and optionally an additive material. The dermatologically-compatible barrier film can also be formed of a composition containing a polysaccharide; a low molecular weight, synergistic saccharide; an antimicrobial; a solvent; and optionally an additive material. The composition is a skin care product in a form of a lotion, a gel, or a cream that is applied to skin of mammals. Once applied, the solvent in the composition evaporates, and thereby leaving behind a dermatologically-barrier film containing polysaccharide; low molecular weight, synergistic saccharide; and optionally an additive material. The film left behind can also contain a polysaccharide; a low molecular weight, synergistic saccharide; an antimicrobial agent; and optionally an additive agent.

The composition of the dermatologically-barrier film is about 14 wt. % to about 87 wt. % of the polysaccharide; about 5 wt. % to about 63 wt. % of the low molecular weight, synergistic saccharide; and optionally about 3 wt. % to 74 wt. % of the additive agent. The composition of the dermatologically-barrier film is about 14 wt. % to about 87 wt. % of the polysaccharide; about 5 wt. % to about 63 wt. % of the low molecular weight, synergistic saccharide; about 0.1 wt. % to 60 wt. % of the antimicrobial agent, and optionally about 3 wt. % to 74 wt. % of the additives.

The dermatologically-barrier film is a non-sticky film that can reduce or inhibit penetration by natural or synthetic allergenic agents or other skin irritants, including non-oily materials such as detergents and constituents of rubber compounds. Advantageously, the film is non-occlusive, non-toxic and flexible. The films are also colorless although colorants can be added if desired. Moreover, the films can avoid powdering and flaking-off during use. The films are also cosmetically acceptable and therefore amenable to formulation into environmental protection skin care (facial) products as well as "invisible glove" products.

The dermatologically-compatible film of the present invention preferably has effective barrier properties. Advantageously, the polysaccharide in the composition has hydrophilic, nonionic, film-forming properties, and some barrier properties. In addition, although the low molecular weight, synergistic saccharide of the present invention by itself does not have film forming or barrier properties, when combined with the film forming polysaccharide of the present invention, the combination produces a more effective film barrier than either component alone. The antimicrobial agent in the composition (1) enhance the preservation of the composition; (2) prevent or reduce infection of open or infected skin when applying the composition; and (3) cleanse skin prior to forming an invisible glove for preventing and reducing contact dermatitis.

While it is not intended to be bound by any one theory, it is believed that the short chains of sugar molecules of the low molecular weight, synergistic saccharide fill the voids in the film created by the much larger polysaccharide, and thereby providing a better film and more effective barrier.

EXAMPLES

The following examples have been set forth as a guide to the practitioner, and are not meant in any way to limit the scope of the present invention. In the following examples, compositions were tested against the following four irritants:

1.3 wt. % pyrocatechol in glycerol 1.3 wt. % 1,4-phenylenediamine in glycerol saturated benzyl disulfide in methanol solution 2.4 wt. % sodium lauryl sulfate in water Film barrier performance of the compositions in the following examples was tested by the Attenuated Total Reflectance-Infrared (ATR-IR) method. In addition, the antimicrobial efficacy of the composition in the following examples was tested by the U.S. Pharmacopeia National Formulary Procedures for Antimicrobial/Preservative Effectoveness and Antibiotics-Microbial Assay.

ATR-IR Method for Measurement of Film Barrier Performance

To a baseline-horizontal, zinc-selenium crystal of the Attenuated Total Reflectance attachment was placed a specific volume of the test solution of the examples. After the solution air-dried to a film, a specific volume of irritant was deposited on top of the dried film. The assembly was placed in a Nicolet Impact Series 400D Fourier-Transform Infrared spectrometer equipped with a deuterated triglycine sulfate detector, Omnic software and operating at 4 cm$^{-1}$ resolution with Happ-Genzel apodization. Infrared spectra were obtained at 30 minute intervals. Selected absorbance bands were monitored for each spectra, depending on the test irritant. These wavelengths were 1521 cm$^{-1}$ for pyrocatechol, 1225 cm$^{-1}$ for sodium lauryl sulfate, 1515 cm$^{-1}$ for 1,4-phenylenediamine, and 1610 cm$^{-1}$ for benzyl disulfide.

The appearance of absorbance bands at the selected wavelengths result from the permeation or penetration of irritant through the dry film. The time at which this occurs is a measure of the protection time period by the barrier formulation being tested. A good correlation exists between this data and clinical tests on humans.

U.S. Pharmacopeia National Formulary Procedures for Antimicrobial/Preservative Effectiveness Twenty milliliters of the sample to be tested is transferred to a sterile tube. The sample is inoculated with a suspension of microorganisms in a ration of 0.1 mL to 20 mL of sample and mixed. The suspension of microorganisms consists of a mixture of gram positive and gram negative bacteria, yeast and mold. The inoculated tubes are incubated at 25 C. for periods of 7, 14, 21 and 28 days. The number of viable organisms is determined at each time-period via plate count. Plate count involves pipetting an aliquot of the sample into a sterile petri dish, adding an appropriate agar growth medium and incubating the petri dish at 37 C. for 24 to 48 hours. The number of viable colonies is then counted and recorded.

U.S. Pharmacopeia National Formulary Procedures for Antibiotics-Microbial Assay Sterile petri dishes containing an appropriate growth medium are prepared and seeded with select microoganisms. The film pellet is deposited on the agar medium and the petri dish is incubated at 37 C. for 24 to 48 hours. The region of non-growth (the zone of inhibition) is measured and recorded.

COMPARATIVE EXAMPLES A TO N

Various compositions of the polysaccharide components and saccharide components by themselves were prepared. The various compositions are shown in Table 1 as Comparative Examples A to N.

This composition was tested against pyrocatechol via the ATR-IR method for measurement of film barrier performance.

The film barrier performance was measured according to the ATR-IR method above using pyrocatechol irritant. 100 or 200 microliters of test solution of the composition was tested against 20 microliters of pyrocatechol irritant.

The results of the ATR-IR method are in Table 1.

TABLE 1

| COMPARATIVE EXAMPLE NO. | Wt. % | CELLULOSIC COMPONENT | | | Wt. % | SACCHARIDE COMPONENT | | | SOLVENT | | Breakthrough |
|---|---|---|---|---|---|---|---|---|---|---|---|
| | | Type | Grade | Supplier | | Type | Grade | Supplier | Wt % | Type | Time (Hr.) |
| A | 0 | | | | 20 | d-fructose | | Aldrich | 80 | Water | 0 |
| B | 0 | | | | 20 | d-glucose | | Aldrich | 80 | Water | 0 |
| C | 0 | | | | 20 | d-sucrose | | Aldrich | 80 | Water | 0 |
| D | 0 | | | | 15 | maltodextrin | | Grain Proc | 85 | Water | 0 |
| E | 0 | | | | 100 | Methyl Gluceth-10 | Glucam E-10 | Amerchol | 0 | | 0.5 |
| F | 0 | | | | 100 | Methyl Gluceth-20 | Glucam E-20 | Amerchol | 0 | | 0.5 |
| G | 0 | | | | 20 | d-maltose | | Aldrich | 80 | Water | 0.5 |
| H | 0 | | | | 20 | d-mannose | | Aldrich | 80 | Water | 0 |
| I | 0 | | | | 20 | corn syrup solids | Maltrin M-250 | Grain Proc | 80 | Water | 0 |
| J | 5 | MC | Methocel A-15LV | Dow Chem | 0 | | | | 95 | Water | 1 |
| K | 15 | HEC | WP-09H | Union Carbide | 0 | | | | 85 | Water | 2 |
| L | 15 | HPC | KLUCEL EF | Aqualon | 0 | | | | 85 | Ethanol | 1 |

TABLE 1-continued

| COMPARATIVE EXAMPLE NO. | Wt. % | CELLULOSIC COMPONENT | | | Wt. % | SACCHARIDE COMPONENT | | | Wt % | SOLVENT Type | Breakthrough Time (Hr.) |
|---|---|---|---|---|---|---|---|---|---|---|---|
| | | Type | Grade | Supplier | | Type | Grade | Supplier | | | |
| M | 20 | HPC | KLUCEL EF | Aqualon | 0 | | | | 80 | Ethanol | 2 |
| N | 5 | HPMC | Methocel K-100 LV | Dow Chem | 0 | | | | 95 | Water | 0.5 |

100 μl test solution was utilized in all Examples with execption of Example J in which 200 μl test solution was utilized.

EXAMPLE 1

Hydroxypropylcellulose (15 grams) (KLUCEL™ EF Grade, Hercules, Inc.) was sprinkled into 80 grams of denatured ethyl alcohol (SDA40) and stirred at room temperature until fully dissolved. Methyl Gluceth-20 (5 grams) (Glucan™ E-20, Amerchol Corp.) was added and the mixture stirred briefly.

This composition was evaluated by the ATR-IR method for barrier performance against several skin irritants and by the clinical method against Rhus extract.

The film barrier performance was measured according to the ATR-IR method described above using all four irritants. 200 microliters of test solution of the composition was tested against 20 microliters of each irritant.

The results of the ATR-IR method show that the above composition provides more than 8 hours of protection time for all irritants.

The clinical method against Rhus extract was performed as follows:

Forearms of five human subjects (known to be allergic to urushiol, the antigen in Rhus extract) were washed with soap and water and towel-dried. Three test solutions of the above compositions were applied (about 0.2 ml each) to three designated 4×4 cm areas in the volar aspect of the subject's forearms. The fourth site was untreated and served as the control.

Using a micropipette, 10 microliter of oleoresin extract standard (1:50 dilution of Rhus oleoresin in ethanol) was applied to 0.6 cm diameter filter paper discs. The discs were allowed to air-dry for 30 minutes and then carefully applied with forceps to each test site. Semi-occlusive tape was placed over each disc. After 8 hours, the discs were removed and the forearms washed with warm water and soap and towel-dried.

The subjects returned to the clinic 72 hours (3 days) later and 120 hours (5 days) for evaluation of dermatitis. This was performed in a blinded fashion using the following 5 point clinical scale:
Score
=0 No Response. Normal skin condition.
=1 Slight Response. Minimally elevated lesions and moderate erythema.
=2 Moderate Response. More elevated lesions with edema and moderate erythema.
=3 Strong Response. Uniformly raised lesions with intense edema, erythema and crusting or scaling.
=4 Very Strong Response. Vesicular reaction.

The result of the clinical method showed that none of the five subjects exhibited an inflammatory response 72 and 120 hours after contact with the urushiol antigen. Positive level—2 inflammatory responses were evident at the control sites (no barrier protection) of all five subjects.

EXAMPLE 2

Hydroxypropylcellulose (15 grams) (KLUCEL™ EF Grade Hercules, Inc.) was sprinkled into 80 grams of distilled water and stirred at room temperature until fully dissolved. D-Fructose (Aldrich Chemical) (5 grams) was added and the mixture stirred until homogenous.

This composition was tested against pyrocatechol via the ATR-IR method for measurement of film barrier performance.

The film barrier performance was measured according to the ATR-IR method above using pyrocatechol irritant. 100 microliters of test solution of the composition was tested against 20 microliters of pyrocatechol irritant.

The results of the ATR-IR method showed that the composition provided more than 8 hours permeation or protection time.

EXAMPLE 3

Hydroxyethylcellulose (15 grams) (CELLOSIZE™ Grade WP-09H, Union Carbide Corporation) was sprinkled into 80 grams of distilled water and stirred at room temperature until fully dissolved. Methyl Gluceth-20 (5 grams) (Glucam™ E-20Amerchol Corporation) was added and the mixture stirred until homogenous.

This composition was tested against pyrocatechol via the ATR-IR method for measurement of film barrier performance.

The film barrier performance was measured according to the ATR-IR method. 100 microliters of test solution of the composition was tested against 20 microliters of pyrocatechol irritant.

The results of the ATR-IR method shows that the composition provided 5 hours permeation or protection time.

EXAMPLES 4 TO 25

Various compositions of the cellulose and saccharide components of the present invention were prepared. The various compositions are shown in Tables 2 and 3.

These compositions were tested against pyrocatechol via the ATR-IR method for measurement of film barrier performance.

The film barrier performance was measured according to the ATR-IR method. 100 or 200 microliters of test solution of the composition was tested against 20 microliters of pyrocatechol irritant.

The results of the ATR-IR method are shown in Tables 2 and 3.

TABLE 2

| EXAMPLE NO. | Wt. % | CELLULOSIC COMPONENT | | | Wt. % | SACCHARIDE COMPONENT | | | SOLVENT | | Breakthrough Time (Hr.) |
|---|---|---|---|---|---|---|---|---|---|---|---|
| | | Type | Grade | Supplier | | Type | Grade | Supplier | Wt. % | Type | |
| 4  | 15 | HPC | KLUCEL EF | Aqualon | 5 | d-fructose | | Aldrich | 80 | Water | >8 |
| 5  | 15 | HPC | KLUCEL EF | Aqualon | 5 | d-glucose | | Aldrich | 80 | Water | 5 |
| 6  | 15 | HPC | KLUCEL EF | Aqualon | 5 | d-mannose | | Aldrich | 80 | Water | >8 |
| 7  | 15 | HPC | KLUCEL EF | Aqualon | 5 | d-sucrose | | Aldrich | 80 | Water | >8 |
| 8  | 15 | HPC | KLUCEL EF | Aqualon | 5 | d-maltose monohydrate | | Aldrich | 80 | Water | 6 |
| 9  | 15 | HPC | KLUCEL EF | Aqualon | 5 | corn syrup sotids | Maltrin M-250 | Grain Proc | 80 | Water | 5 |
| 10 | 15 | HPC | KLUCEL EF | Aqualon | 5 | maltodextrin | Maltrin M-180 | Grain Proc | 80 | Water | >8 |
| 11 | 15 | HPC | KLUCEL EF | Aqualon | 5 | PPG-10 MeGlu ether | Glucam P-10 | Amerchol | 80 | Ethanol | 5 |
| 12 | 15 | HPC | KLUCEL EF | Aqualon | 5 | PPG-20 MeGlu ether | Glucam P-20 | Amerchol | 80 | Ethanol | 5.5 |
| 13 | 15 | HPC | KLUCEL EF | Aqualon | 5 | MeGluceth-20 Distearate | Glucam E-20 distear. | Amerchol | 80 | Ethanol | 2 |
| 14 | 15 | HPC | KLUCEL EF | Aqualon | 5 | MeGlu Dioleate | Grillocose DO | RITA | 80 | Ethanol | 4.5 |
| 15 | 15 | HPC | KLUCEL EF | Aqualon | 5 | MeGlu Sesquistearate | Grillocose IS | RITA | 80 | Ethanol | 1 |
| 16 | 15 | HPC | KLUCEL EF | Aqualon | 5 | PPG-20 MeGlu ether | Glucam P-20 distear. | Amerchol | 80 | Ethanol | 3 |
| 17 | 15 | HPC | KLUCEL EF | Aqualon | 5 | sucrose shearate | Grilloten PSE 141G | RITA | 80 | Ethanol | 0 |
| 18 | 15 | HPC | KLUCEL EF | Aqualon | 5 | Methyl Gluceth-20 | Glucam E-20 | Amerchol | 40 + 40 | Water + Ethanol | 5.5 |

100 μl of test sotution was utilized in all Examples

TABLE 3

| EXAMPLE NO. | Wt. % | CELLULOSIC COMPONENT | | | Wt. % | SACCHARIDE COMPONENT | | | Wt. % | SOLVENT | Breakthrough Time (Hr.) |
|---|---|---|---|---|---|---|---|---|---|---|---|
| | | Type | Grade | Supplier | | Type | Grade | Supplier | | Type | |
| 19 | 5  | MC   | Methocel A-15 LV  | Dow Chem | 5 | Methyl Gluceth-20 | Glucam E-20 | Amerchol | 90 | Water | 5 |
| 20 | 15 | EC   | Ethocel           | Dow Chem | 5 | Methyl Gluceth-20 | Glucam E-20 | Amerchol | 80 | Ethanol | >8 |
| 21 | 15 | HEC  | WP-O9H            | Union Carbide | 5 | Methyl Gluceth-20 | Glucam E-20 | Amerchol | 80 | Water | 5 |
| 22 | 15 | HPC  | KLUCEL/EF         | Aqualon | 5 | Methyl Gluceth-10 | Glucam E-10 | Amerchol | 80 | Ethanol | 5 |
| 23 | 15 | HPC  | KLUCEL EF         | Aqualon | 5 | Methyl Gluceth-20 | Glucam E-20 | Amerchol | 80 | Ethanol | 5 |
| 24 | 5  | HPMC | Methocel K-100 LV | Dow Chem | 5 | Methyl Gluceth-20 | Glucam E-20 | Amerchol | 90 | Water | 1.5 |
| 25 | 10 | CMC  | Cell Gum 7L2P     | Aqualon | 5 | Methyl Giuceth-20 | Methyl Gluceth-20 | Amerchol | 85 | Water | 0.5 |

100 μl of test solution was utilized in all Examples with exception of Example 19 in which 200 μl test solution was utilized.

As demonstrated in Tables 2 and 3, the combination of a polysaccharide, i.e., a cellulose derivative, and a low molecular weight, synergistic saccharide provides a dermatologically-compatible barrier film having excellent barrier properties. More specifically, Example 4 in Table 2 shows that the combination of 15 wt. % HPC and 5 wt. % d-fructose in 80 wt. % water provides more than 8 hours of protection time against pyrocatechol irritant. In contrast, 15 wt. % HPC in 85 wt. % ethanol provides only 1 hour of protection time (Comparative Example L in Table 1). In addition, 20 wt. % d-fructose in 80 wt. % water does not provide any protection time whatsoever (Comparative Example A).

Similarly, Example 19 in Table 3 demonstrates that the combination of 5 wt. % Methyl Cellulose (MC) and 5 wt. % Methyl Gluceth-20 in 90 wt. % water provides 5 hours of protection time. In contrast, 5 wt. % MC in 95 wt. % of water only provides 1 hour of protection time (Comparative Example J). In addition, 100 wt. % Methyl Gluceth-20 provides 0.5 hours or less of protection time (Comparative Example F).

Furthermore, Example 21 in Table 3 shows that the combination of 15 wt. % HEC and 5 wt. % Methyl Gluceth-20 in 80 wt. % water provides 5 hours of protection time against pyrocatechol irritant. In contrast, 15 wt. % HEC in 85 wt. % water provides only 2 hour of protection time (Comparative Example K in Table 1). In addition, 100 wt. % Methyl Gluceth-20 by itself provides 0.5 hour or less of protection time (Comparative Example F).

Tables 1 to 3 clearly demonstrate that the low molecular weight, synergistic saccharide of the present invention by itself has substantially no film-forming or barrier properties. However, when the low molecular weight, synergistic saccharide is combined with the film-forming polysaccharide of the present invention, the combination unexpectedly provides a more effective film barrier than either component alone.

EXAMPLE 26

Hydroxypropylcellulose (30 grams) (KLUCEL™ EF Grade, Aqualon Company), Methyl Gluceth-20 (10 grams) (Glucam™ E-20, Amerchol Corp.), and triclosan (0.6 gram) (IRGASAN™ DP 300 ) and 159.4 grams SD Alcohol 40 were mixed in a 250 ml NALGENE bottle to form a homogenous mixture.

Two hundred microliters of the formulation were dried to a film pellet at 80° C. in a draft oven for the Antibiotics-Microbial Assay in accordance with the U.S. Pharmacopeia National Formulary Procedures. The results showed that the films tested exhibited activity against gram positive and gram negative bacteria and yeast.

For the ATR-IR test, 100 microliters of the formulation was deposited onto a ZnSe crystal and air-dried. The film barrier performance was measured according to the ATR-IR method above using 20 microliters of pyrocatechol irritant. The results of the ATR-IR method showed that the composition provided 5 hours permeation or protection time.

EXAMPLE 27

Hydroxypropylcellulose (30 grams) (KLUCEL™ EF Grade, Aqualon Company), Methyl Gluceth-20 (10 grams) (Glucam™ E-20, Amerchol Corp.), and 0.2 gram of DOWICIL™ 200 were mixed in distilled water (159.8 grams) to form a homogenous mixture.

The formulation was tested for antimicrobial/preservatives-effectiveness according to U.S. Pharmacopeia National Formulary Procedures against a pool of microorganisms, including gram positive and gram negative bacteria, yeast and mold.

Twenty milliliters of the sample was inoculated with 0.1 ml of a suspension of microorganisms and incubated at 25° C. for 7, 14, 21, and 28 days. Aliquots of the inoculated sample were plated out to determine the number of viable organisms. The results showed that the formulation remained free of any detectable organisms following several cycles of testing.

For the ATR-IR test, 100 microliters of the test solution of the composition were tested against 20 microliters of pyrocatechol irritant The results of the ATR-IR method showed that the composition provided 5.5 hours permeation or protection time.

While there have described what are believed to be the preferred embodiments of the invention, those skilled in the art will realize that changes and modification may be made thereto without departing from the spirit of the invention, and it is intended to claim all such changes and modifications are fall within the true scope of the invention.

What is claimed is:

1. A dermatologically-compatible barrier film comprising:
   (1) a polysaccharide;
   (2) a low molecular weight, synergistic saccharide; and
   (3) optionally an additive agent.

2. The dermatologically-compatible barrier film of claim 1 further comprises an antimicrobial agent.

3. The dermatologically-compatible barrier film of claim 1, wherein said polysaccharide is a cellulose derivative.

4. The dermatologically-compatible barrier film of claim 1, wherein said cellulose is selected from the group consisting of methylcelluclose, ethylcellulose, hydroxyethylcellulose, hydroxypropylcellulose, hydroxybutylcellulose, methylhydroxyethylcellulose, methylhydroxypropylcellulose, methylhydroxybutylcellulose, hydroxyethylhydroxypropylcellulose, and ethylhydroxyethylcellulose.

5. The dermatologically-compatible barrier film of claim 1, wherein said polysaccharide is hydroxypropylcellulose.

6. The dermatologically-compatible barrier film of claim 1, wherein said synergistic saccharide is selected from the group consisting of unmodified monosaccharide, derivatized monosaccharide, unmodified disaccharide, derivatized disaccharide, hydrolyzed starch, and derivatized starch hydrolysate.

7. The dermatologically-compatible barrier film of claim 6, wherein said unmodified monosaccharide is selected from the group consisting of fructose, glucose, and mannose.

8. The dermatologically-compatible barrier film of claim 6, wherein said unmodified disaccharide is selected from the group consisting of sucrose and maltose.

9. The dermatologically-compatible barrier film of claim 6, wherein said derivatized monosaccharide is selected from the group consisting of ethoxylates of methyl glucoside, propoxylates of methyl glucoside, propoxylates of methyl glucoside disterate, and methyl glucose doleate.

10. The dermatologically-compatible barrier film of claim 6, wherein said derivatized monosaccharide is about 20 mole ethoxylate of methyl glucoside.

11. The dermatologically-compatible barrier film of claim 6, wherein said hydrolyzed starch is selected from the group consisting of maltodextrin and corn syrup solids.

12. The dermatologically-compatible barrier film of claim 1, wherein said additive agent is selected from the group consisting of colorants, fragrances, sunscreen, insect repellants, surfactants, flow modifiers, cleansers, moisturizers, water resistant compounds, salts, natural extracts, exfoliants, astringents, antioxidants, vitamins, self-tanning gents, emulsifiers, emollients, enzymes, keratolytics, antipruitics, analgesics, anesthetics, antihistamines, antimicrobial agents, preservatives, antibiotics, antiseptics, antifunals, antivirals, and mixtures thereof.

13. The dermatologically-compatible barrier film of claim 1, wherein said polysaccharide is in the amount of 14 wt. % to 87 wt. % wherein said low molecular weight, synergistic saccharide is in the amount of 5 wt. % to 63 wt. %, and optionally wherein said additive agent is in the amount of about 37 wt. % to about 74 wt. %.

14. The dermatologically-compatible barrier film of claim 2, wherein said antimicrobial agent is selected from the group consisting of triclosan, hexetidine, chlorhexidine salts, 2-bromo-2-nitropropane-1,3-diol, hexyresorcinol, benzalkonium chloride, cetylpyridinium chloride, alkylbenzyldimethylammonium chlorides, iodine, phenol derivatives, povidone-iodine, parabens, hydantoins, hydantoin derivatives, phenoxyethanol, cis isomer of 1-(3-chloroallyl)-3,5,6-triaza-1-axoniaadamantane chloride, diazolidinyl urea, benzethonium chloride, methylbenzethonium chloride, and mixtures thereof.

15. The dermatologically-compatible barrier film of claim 2, wherein said antimicrobial agent is selected from the group consisting of triclosan, cis isomer of 1-(3-chloroallyl)-3,5,6-triaza-1-azoniaadamantane chloride, hydantoins, hydantoin derivatives, and mixtures thereof.

16. The dermatologically-compatible barrier film of claim 2, wherein said polysaccharide is in the amount of 14 wt. % to 87 wt. %, wherein said low molecular weight, synergistic saccharide is in the amount of 5 wt. % to 63 wt. %, wherein said antimicrobial agent is in the amount of about 0.1 wt. % to about 60 wt. %, and optionally wherein said additive agent is in the amount of about 37 wt. % to about 74 wt. %.

* * * * *

UNITED STATES PATENT AND TRADEMARK OFFICE
CERTIFICATE OF CORRECTION

PATENT NO. : 6,110,475
DATED : August 29, 2000
INVENTOR(S) : Toma et al.

It is certified that error appears in the above-identified patent and that said Letters Patent are hereby corrected as shown below:

In the Title, "COMPOSTION" should read --COMPOSITION--;

Table 2, Row No. 9, "sotids" should read --solids--.

Signed and Sealed this

Fifteenth Day of May, 2001

*Attest:*

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO. : 6,110,475
DATED : August 29, 2000
INVENTOR(S) : Toma et al.

It is certified that error appears in the above-identified patent and that said Letters Patent is hereby corrected as shown below:

<u>Title page,</u>
Item [54], "COMPOSTION" should read -- COMPOSITION --;

<u>Columns 11 and 12,</u>
"sotids" should read -- solids --.

Signed and Sealed this

Twenty-first Day of September, 2004

JON W. DUDAS
*Director of the United States Patent and Trademark Office*